United States Patent [19]
Epstein

[11] Patent Number: 5,906,814
[45] Date of Patent: May 25, 1999

[54] TOPICAL FILM-FORMING COMPOSITIONS

[75] Inventor: Howard Epstein, Rochester, N.Y.

[73] Assignee: The Andrew Jergens Company, Cincinnati, Ohio

[21] Appl. No.: 08/735,352

[22] Filed: Oct. 22, 1996

Related U.S. Application Data

[60] Provisional application No. 60/008,333, Dec. 7, 1995.

[51] Int. Cl.$^6$ ........................................................ A61K 7/48
[52] U.S. Cl. ........................ 424/78.02; 424/401; 514/886; 514/887; 514/944
[58] Field of Search ..................................... 424/401, 443, 424/444, 448, 78.08; 514/886, 887, 944

[56] References Cited

U.S. PATENT DOCUMENTS

| | | |
|---|---|---|
| Re. 33,093 | 10/1989 | Schiraldi et al. . |
| 3,899,580 | 8/1975 | O'Neill et al. . |
| 4,285,934 | 8/1981 | Tinnell . |
| 4,381,296 | 4/1983 | Tinnell . |
| 4,474,753 | 10/1984 | Haslam et al. . |
| 4,478,853 | 10/1984 | Chaussee . |
| 4,713,243 | 12/1987 | Schiraldi et al. . |
| 4,746,515 | 5/1988 | Cheng et al. ............................ 424/449 |
| 4,789,667 | 12/1988 | Makino et al. . |
| 4,895,727 | 1/1990 | Allen . |
| 4,952,560 | 8/1990 | Kigasawa et al. . |
| 4,954,487 | 9/1990 | Cooper et al. . |
| 4,963,591 | 10/1990 | Fourman et al. . |
| 4,970,220 | 11/1990 | Chaussee . |
| 5,081,157 | 1/1992 | Pomerantz . |

FOREIGN PATENT DOCUMENTS 2179858  3/1987  United Kingdom .

OTHER PUBLICATIONS

Pomerantz, "Protective film for body tissues containing hydroxypropyl cellulose and weak carboxylic acids", Chemical Abstracts, 113:103460f, 1990, p. 402.

Rodu, "Clinical and chemical properties of a novel muscosal bioadhesive agent", Chemical Abstracts, 111:681H, 1989, p. 64.

Morton, "Compositions for treating viral skin diseases", Chemical Abstracts, 107:121102w, 1987, p. 354.

*Primary Examiner*—Jyothsna Venkat
*Attorney, Agent, or Firm*—Oblon, Spivak, McClelland, Maier & Neustadt, P.C.

[57] ABSTRACT

The present invention is a topical film-forming composition comprising; (a) a non-toxic volatile solvent, (b) a cellulosic material having at least one hydroxyl group on a side chain of a cellulose backbone, (c) an esterification agent capable of reacting with said hydroxyl group on the side chain of said cellulosic material to form an ester, and (d) a glycerol monolaurate crosslinking agent. Various medicinal, antibiotic, anitfungal, anesthetic, analgesic and virucidal agents may be included within the composition.

7 Claims, No Drawings

TOPICAL FILM-FORMING COMPOSITIONS

This application claims the benefit of U.S. Provisional Application No(s) 60/008,333, filed Dec. 7, 1995, now abandoned.

FIELD OF THE INVENTION

The present invention relates to topical film-forming compositions for direct application to body tissues in the treatment of various tissue aliments. In one application, the subject compositions are used in the treatment of orofacial lesions including canker sores and cold sores. Other applications include the treatment of chapped lips, fever blisters, burns, cuts, and abrasions.

BACKGROUND

Topical film-forming compositions are commonly used in the treatment of various tissues aliments including cold sores, canker sores, chapped lips, burns, cuts, abrasions, etc. Such compositions are designed to form a protective film over the tissue area of application. Furthermore, these compositions may serve as carriers for various medicinal, antibiotic, antifungal, anesthetic, analgesic and virucidal agents as well as related components such as penetration enhancers (e.g. AZONE). Examples of such film-forming compositions include those disclosed in U.S. Pat. Nos. 4,381,296 and 4,285,934 both to Tinnell, Re. 33,093 to Schiraldi et al., and 5,081,157 to Pomerantz.

The effectiveness of topical film-forming compositions is highly dependent upon the mechanical properties of the film ultimately formed upon the tissue site. That is, to be effective, film-forming compositions must be capable of adhering to tissues, including moist mucosal tissue, e.g. as in oral applications. Furthermore, the resultant film must resist abrasion and irrigation by body fluids. Perhaps most importantly, such films must be flexible, as the tissues to which they are adhered to, stretch and flex.

One class of known film-forming compositions use ethyl cellulose film-formers with esterification agents. These compositions tend to produce brittle films which are likely to separate from their sites of application. While not wishing to be bound by theory, it is believed that the brittle nature of these films is a result of the use of ethyl cellulose, which only undergoes esterification at sites on the cellulose backbone.

Another class of known film-forming compositions utilize hydroxypropyl cellulose with esterifications agents. These compositions do not exhibit the same degree of brittleness, as with ethyl cellulose. This is believed to be due to the presence of hydroxyl groups on side chains from the cellulose backbone, which are capable of esterification. One drawback to these compositions, however, is that they tend to be relatively weak and often do not maintain their integrity. As such, films formed from such compositions are commonly displaced shortly after their application. The addition of crosslinking agents to these compositions can increase the strength of films formed thereby, but such crosslinking can render the film quite brittle.

For example, U.S. Pat. No. 5,081,157 to Pomerantz discloses a topical film-forming composition which includes: 1) hydroxypropyl cellulose, 2) a non-toxic volatile solvent, e.g. an alcohol, 3) an esterification agent, e.g. a carboxylic acid, 4) a boric acid crosslinking agent, and 5) medicinal compounds, e.g. hydrocortisone, lidocaine hydroclholoride, benzocaine, etc. As described in the reference, the carboxyl groups of the esterification agent (e.g. tannic acid and salicyclic acid) undergo esterification with the hydroxypropyl cellulose. Following and/or during esterification, boric acid crosslinks parts of the ester. This crosslinking adds strength to the resulting film; however, since boric acid has three hydroxyl groups, it is capable of crosslinking the ester at three locations. These three locations are only separated by an interstitial boron atom. Although not wishing to be bound by theory, it is believed that the crosslinked portions of the ester(s) are drawn too close together due to the close proximity of the three hydroxyl groups of boric acid, thus forming a rigid opaque film. As a result, the film formed tends to be thick and brittle, causing it to frequently crack and dislodge from its point of application. Furthermore, compositions including boric acid are known to cause skin irritation for many individuals.

Thus, strong, yet flexible, non-irritating film-forming compositions are sought which readily adhere to moist tissues.

SUMMARY OF THE INVENTION

The present invention is a topical, non-irritating, film-forming composition for treating various tissue aliments. The composition comprises; (a) a non-toxic volatile solvent, (b) a cellulosic material having at least one hydroxyl group on a side chain of a cellulose backbone, (c) an esterification agent capable of reacting with the hydroxyl group on the side chain of the cellulosic material to form an ester, and (d) a glycerol monolaurate crosslinking agent.

The subject composition is effective in treating body tissues by forming a strong, yet flexible topical film which readily adheres to body tissues, including moist oral tissues. The subject composition may include various medicinal, antibiotic, anitfungal, anesthetic, analgesic and virucidal agents. In preferred embodiments, the subject composition specifically avoids the use of boric acid.

DETAILED DESCRIPTION OF THE INVENTION

As previously stated, the present invention is a topical film-forming composition comprising; (a) a non-toxic volatile solvent, e.g. an alcohol, water, etc., (b) a cellulosic material having at least one hydroxyl group on a side chain of a cellulose backbone, e.g. hydroxypropyl cellulose, (c) an esterification agent capable of reacting with the hydroxyl group on the side chain of the cellulosic material to form an ester; e.g. a carboxylic acid, and (d) glycerol monolaurate as a crosslinking agent. The subject composition may also include various medicinal, antibiotic, anitfungal, anesthetic, analgesic and virucidal agents, as described below.

The cellulosic materials applicable to the present invention must have at least one side chain extending from a cellulose backbone. Furthermore, the side chain must include at least one hydroxyl group. Specific examples of suitable materials include hydroxypropyl cellulose, hydroxypropyl methyl cellulose, hydroxypropyl ethyl cellulose, dextran, guaran, resin Jalap, and mixtures thereof. A particularly preferred material is a hydroxypropyl cellulose available from Aqualon Co. of Wilmington, Del. under the name KLUCEL HF.

The esterifications agents useful in the present invention including organic acids, e.g. carboxylic acids, capable of undergoing an esterification reaction with the hydroxyl group on the side chains of the cellulosic material. Preferred esterifications agents include salicyclic acid, tannic acid, acetic acid and mixtures thereof. Salicylic acid is particularly preferred as it does not impart a color to the resulting film when applied. In addition to undergoing esterification with cellulosic materials (and possibly hydrogen bonding with hydroxyl groups of glycerol monolaurate, as described below), salicylic acid may contribute to the overall virucidal efficacy of the composition. When using hydroxypropyl cellulose and salicylic acid, the esterification reaction can be represented as follows:

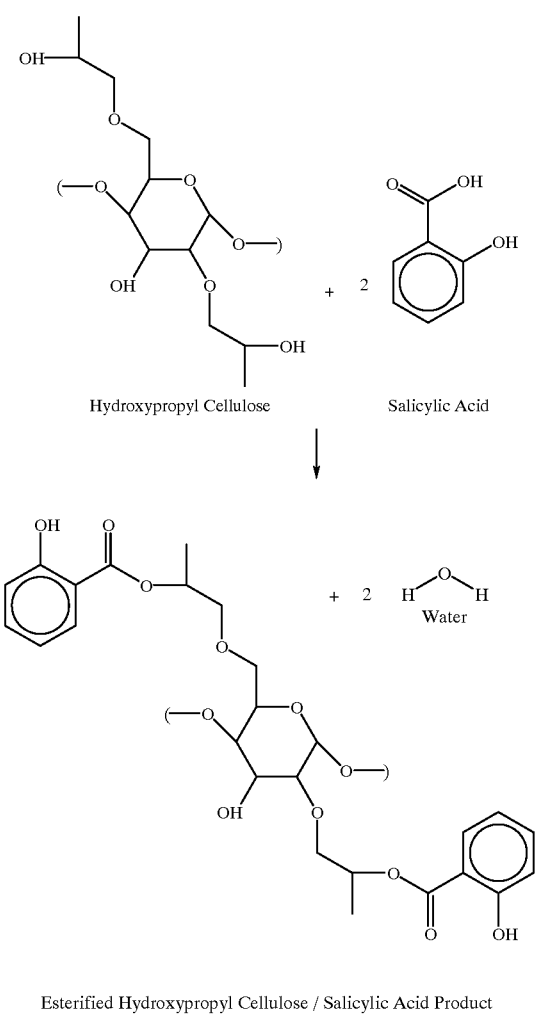

Hydroxypropyl Cellulose   Salicylic Acid

Esterified Hydroxypropyl Cellulose / Salicylic Acid Product

The crosslinking agent of the present invention comprises glycerol monolaurate. Glycerol monolaurate, when used in combination with the esterification agent and cellulose materials of the present invention, creates a film having greater flexibility than that of other known topical compositions. Although not wishing to be bound by theory, it is believed that, upon associating with the esterfied cellulosic material, glycerol monolaurate creates a particularly flexible film due to the relative spacing of hydroxyl groups and the overall size of the molecule. This is generally illustrated below, (with hydrogen bonding shown as dotted lines).

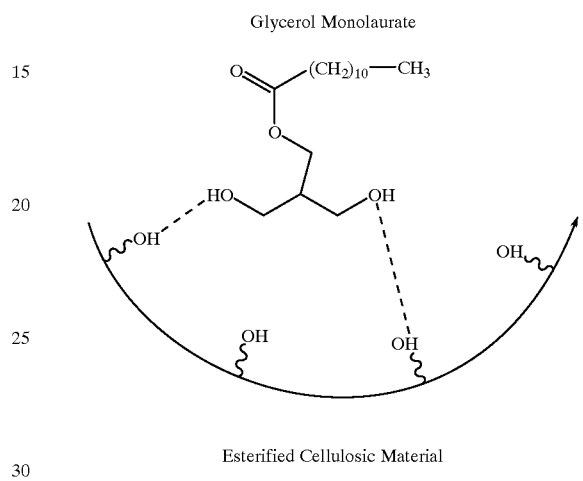

Glycerol Monolaurate

Esterified Cellulosic Material

Following and during esterification, hydrogen bonding is believed to occur between the free hydroxyl groups on the cellulose backbone of the esterified cellulosic material and glycerol monolaurate. It is also possible that such hydrogen bonding takes place between hydroxyl groups originally present on the esterification agent and those of the glycerol monolaurate. This is specifically illustrated below with respect to glycerol monolaurate and the esterified hydroxypropyl cellulose/salicylic acid product, (wherein hydrogen bonding is indicated with dotted lines).

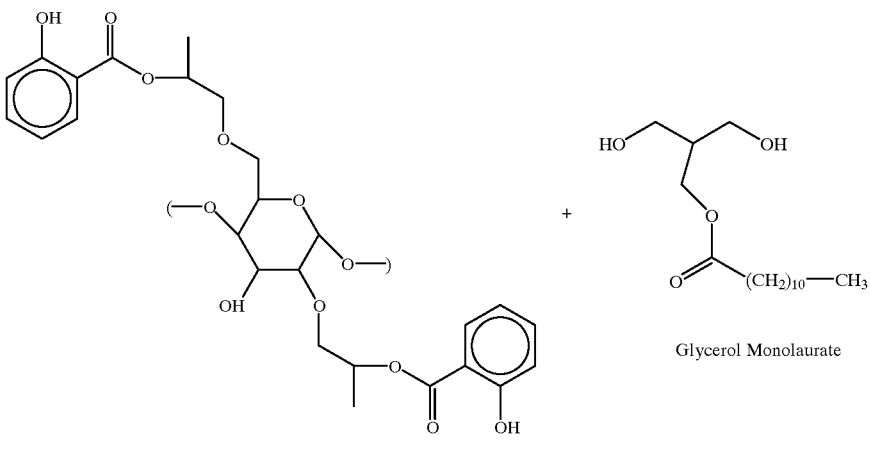

Esterified Hydroxypropyl Cellulose / Salicylic Acid Product

Glycerol Monolaurate

-continued

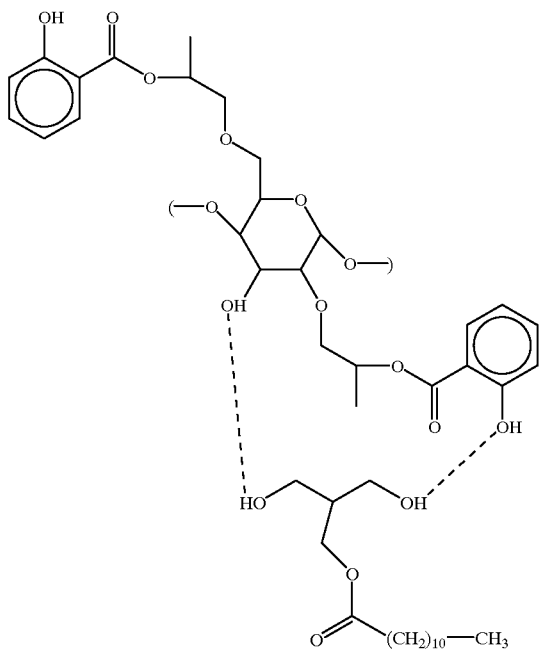

Esterified Hydroxypropyl Cellulose and Salicylic Acid Product
crosslinked to Glycerol Monolaurate In addition to serving as crosslinking agent, glycerol monolaurate also may contribute to the virucidal activity of the composition.

Other crosslinking agents and/or crosslinking control agents may be used in combination with glycerol monolaurate. For the purposes of this discussion, the term crosslinking agent refers to compounds capable of forming a plurality of simultaneous hydrogen bonds with the esterification product (i.e. the esterified cellulose material). Specific examples of additional crosslinking agents include glycerol, polyethylene glycol and mixtures thereof. Crosslinking control agents refer to compounds capable of forming only one hydrogen bond with esterified product. Crosslinking control agents are particularly helpful as they act to "tie-up" potential crosslinking sites of the esterified product, thus helping control the degree of crosslinking in the resulting film. Specific examples of crosslinking control agents include benzyl alcohol, phenol, hexanol and mixtures thereof.

Crosslinking agents and crosslinking control agents including a ballast moiety having a molecular weight of at least about 40 have been found to be preferred. For purposes of this discussion, the ballast moiety constitutes the entire crosslinking agent and/or crosslinking control agent, but for the groups (e.g., hydroxyl) available for hydrogen bonding. A variety of suitable ballast moieties can be utilized. One type of suitable ballast moiety is an aryl group having one or more aromatic rings. Another type of suitable ballast moiety is an aliphatic group, substituted or unsubstituted. Suitable substituents include amine, carboxyl, aldehyde, ketone, and acid derivatives of carboxylic acids. Moieties with long chain lengths or significant side chains are less preferred, as their groups available for hydrogen bonding are less reactive.

It is believed that the ballast groups of the aforementioned crosslinking agents and/or crosslinking control agents impart steric hindrance between portions of one or more ester chains. This in turn is believed to increase the distance between areas of crosslinking.

The composition preferably excludes boric acid. Although boric acid is effective at crosslinking the esterified cellulose product, it nonetheless creates a film which is brittle and tends to crack. Although not wishing to be bound by theory, it is believed that boric acid crosslinks portions of the ester(s) in such a manner as to draw them close together, thus forming a rigid opaque film. As a result, the film tends to be thick and brittle, causing it to frequently crack and dislodge from its point of application. Furthermore, compositions including boric acid are known to cause skin irritation for many individuals.

The aforementioned constituents of the subject film-forming compositions are blended with a non-toxic volatile solvent which carries the various constituents and helps form a film over an area of application. Preferred solvents are those which evaporate under ambient conditions so that, upon application of the composition, the solvent is removed and a film is formed. Suitable solvents include alcohols, e.g. ethyl alcohol (preferably denatured, isopropyl alcohol, methyl alcohol, water and combinations thereof The solvent should be non-toxic for the intended application of the composition. As such, in oral applications, some alcohols may not be appropriate solvents.

Various medicinal, antibiotic, anitfungal, anesthetic, analgesic and virucidal agents, along with other components such as penetration enhancers may be added to the composition, as is known in the art. Examples of such preferred analgesic agents include; tetracaine, benzocaine, lidocaine, and mixtures thereof Examples of preferred virucidal agents include; phenyl phenol, glutaraldehyde and mixtures thereof Other examples of known agents are disclosed in U.S. Pat. No. 5,081,157 to Pomerantz.

Typically, compositions of the present invention include from about 0.1 to 2.5 weight percent cellulosic material, about 0.9 to 7 weight percent esterification agent, about 0.1 to 8 weight percent glycerol monolaurate, optionally about 0.5 to 20 weight percent analgesic, and optionally about 0.5 to 5 weight percent of a virucidal agent. The remaining portions of the composition constitute solvent and other optional additives. For example, if crosslinking control agents or other additional crosslinking agents are used, they are typically used in amounts wherein the total weight percent of the glycerol monolaurate, additional crosslinking agents, and crosslinking control agents do not collectively exceed about 30 weight percent. Typically, the amount of crosslinking control agent, if used, is about 0.5 to 16 weight percent.

The composition should preferably have a viscosity of about 40,500 to about 122,000 centipoise, and preferably about 120,000 centipoise. The composition preferably has a pH value of from about 2.5 to about 6.0, and more preferably about 4.0. The specific gravity of the composition is preferably about 0.81 to about 0.85.

In use, the composition of the present invention can be applied by spraying, dipping, swab, etc., effected tissue areas, thus forming a thin layer of gel thereover. Once the solvent in the composition evaporates, the gel dries to form a thin, flexible film.

The composition of the present invention is a substantial advance in topical film-forming compositions due to the improved flexibility of the resulting film. The present invention is particularly useful in treating various tissue aliments, including cold sores, fever blisters, and canker sores. The present composition may be used around the mouth area without being dislodged by movement of the mouth and without being visible. With additives having analgesic and virucidal activity, the present invention is able to promote healing, provide quick and long lasting pain relief, and achieve long lasting protection without skin irritation.

EXAMPLES

As a further illustration of the invention, several examples of the subject film-forming compositions were prepared. The specific formulations for each example are provided below in TABLE I. Each of the example formulations were prepared by adding ethyl alcohol to an explosion-proof tank or suitable vessel equipped with an appropriate agitator. With moderate mixing by the agitator, the remaining ingredients were each individually added to the tank in any order provided each ingredient was completely dissolved before the next was added. (It is particularly important to insure that the cellulose material is fully dissolved with no lumps in the final product.)

TABLE I

| Constituent | Gel A | Gel B | Gel C | Gel D |
| --- | --- | --- | --- | --- |
| Ethyl Alcohol (190%) | 80.0 | 80.2 | 80.0 | 80.35 |
| Hydroxypropyl Cellulose NF | 1.9 | 1.5 | 1.8 | 1.5 |
| Salicyclic Acid USP | 2.0 | 1.0 | 1.0 | 2.0 |
| Glycerol Monolaurate | 5.0 | 0.5 | 0.5 | 5.0 |
| Benzocain USP | 10.5 | | | 10.0 |
| Tetracaine HCL USP | | 1.0 | 1.0 | |
| BHT in Corn Oil | 0.10 | 0.08 | 0.1 | |

TABLE I-continued

| Constituent | Gel A | Gel B | Gel C | Gel D |
| --- | --- | --- | --- | --- |
| Phenol USP | 0.5 | 0.5 | 0.5 | |
| Disodium EDTA | | | | 0.05 |
| Vitamin E | | | | 0.1 |
| Benzyl Alcohol USP | | 15.0 | | |
| Propylene Glycol USP | | | 10.1 | |
| Water, Purified USP | | | 5.0 | |

Gels A, B, and C were tested with a number of subjects having canker sores and/or cold sores. The gels were test by having each subject apply a small amount of gel to their effected tissue areas. The subjects were then asked to report their impressions of the gel. The subjects generally reported reduced pain associated with cold and/or canker sores when treated with the subject gel. Furthermore, the subjects typically reported that the duration of their canker sores and cold sores was less when treated with the subject gel.

Many other modifications and variations of the present invention are possible in light of the teachings herein. It is therefore understood that, within the scope of the claims, the present invention can be practiced other than as herein specifically described.

I claim:

1. A method for treating a tissue ailment selected from the group consisting of cold sores, fever blisters, and canker sores, by applying a topical film-forming composition to an affected tissue area, wherein the film-forming composition comprises:

(a) a non-toxic volatile solvent;
    (b) a cellulosic material having at least one hydroxyl group on a side chain of a cellulose backbone;
    (c) an esterification agent capable of reacting with said hydroxyl group on the side chain of said cellulosic material to form an ester; and
    (d) glycerol monolaurate; wherein the composition excludes boric acid.

2. The method of claim 1 wherein the solvent includes at least one of: ethyl alcohol, isopropyl alcohol, methyl alcohol, and combinations thereof.

3. The method of claim 1 wherein said cellulosic material includes at least one of: hydroxypropyl cellulose, hydroxypropyl methyl cellulose, and combinations thereof.

4. The method of claim 1 wherein the esterification agent includes at least one of: salicylic acid, tannic acid, acetic acid, and combinations thereof.

5. The method of claim 1 wherein the composition further comprises at least one of: an analgesic agent, a virucidal agent, and combinations thereof.

6. The method of claim 1 wherein the composition comprises about 0.1 to 2.5 weight percent of said cellulosic material, about 0.9 to 7 weight percent of said esterification agent, and about 0.1 to 8 weight percent of said glycerol monolaurate.

7. The method of claim 1 wherein the composition includes a crosslinking control agent.

* * * * *